United States Patent [19]

Kounaves et al.

[11] Patent Number: 5,378,343
[45] Date of Patent: Jan. 3, 1995

[54] ELECTRODE ASSEMBLY INCLUDING IRIDIUM BASED MERCURY ULTRAMICROELECTRODE ARRAY

[75] Inventors: Samuel P. Kounaves, Winchester, Mass.; Gregory T. A. Kovacs, Stanford; Christopher W. Storment, Cupertino, both of Calif.

[73] Assignees: Tufts University, Medford, Mass.; Leland Standard Univ., Stamford, Calif. ; a part interest

[21] Appl. No.: 3,229

[22] Filed: Jan. 11, 1993

[51] Int. Cl.⁶ ............................................. G01N 27/26
[52] U.S. Cl. ................................... 204/413; 204/412; 204/290 R; 204/435
[58] Field of Search .................. 204/290 R, 413, 435, 204/153.23, 412

[56] References Cited

U.S. PATENT DOCUMENTS 5,120,421 6/1992 Glass et al. ........................ 204/406

OTHER PUBLICATIONS

Kounaves et al., J. Electroanal. Chem. vol. 301, pp. 77-85 (1991) no month presently available.
Kovacs, Technology Development for a Chronic Neural Interface, Ph.D. Dissertation, Stanford University, Technical Report No. E073-1, pp. 87-100 (Aug. 1990).
Kovacs, Proceedings of the 12th International Conference of the Assoc. for the Advanc. of Rehab. Techn., New Orleans, La., pp. 292-293 (Jun. 1989).

*Primary Examiner*—John Niebling
*Assistant Examiner*—Bruce F. Bell
*Attorney, Agent, or Firm*—Kriegsman & Kriegsman

[57] ABSTRACT

An electrode assembly for use in quantifying the levels of various metals in an aqueous solution. In one embodiment, the electrode assembly comprises a substrate, the substrate being a silicon chip upon which a layer of silicon dioxide has been grown. A plurality of gold bond pads and gold interconnect traces are deposited by microphotolithography onto the silicon dioxide layer. An array of iridium deposits are then patterned by microphotolithography onto the interconnect traces at predefined locations. A passivation layer is deposited by plasma enhanced chemical vapor deposition over the finished metallization to electrically insulate it from external solutions. Plasma etching is then used to expose at least a portion of each of the iridium deposits. Just prior to analytical use, one or more of the exposed iridium elements are electroplated with mercury. The present invention is also directed to a field deployable sensor including the above-described electrode assembly.

24 Claims, 6 Drawing Sheets

FIG. I

ELECTRODE ASSEMBLY INCLUDING IRIDIUM BASED MERCURY ULTRAMICROELECTRODE ARRAY

BACKGROUND OF THE INVENTION

The present invention relates generally to electrodes and more particularly to a new and novel electrode assembly for use in quantifying the levels of various metals in an aqueous solution.

One of the most sensitive techniques presently known for measuring the concentration of various heavy metals in water is anodic stripping voltammetry (ASV). ASV typically comprises a two step process wherein (1) a negative potential is applied at a small film or drop of mercury so that the metal ions in solution are electrochemically reduced and concentrated into the mercury; and (2) after a period of time, the applied potential is slowly scanned in the positive direction, resulting in a peak current at the oxidation potential of each metal proportional to its concentration.

The critical component of this technique is the mercury drop or film electrode. There have been two types of electrodes used with ASV, the hanging-mercury-drop (HMDE) and the mercury-film (MFE). The HMDE is typically a less than 1 mm in diameter drop of mercury suspended from a glass capillary. The problems associated with using the HMDE include the undesirability of working with bulk mercury, its relative "massiveness" with respect to internal diffusion leading to low resolution or prolonged analysis times, and the uncontrolled solution hydrodynamics and diffusion at its surface during the deposition step.

The MFE consists of a flat inlaid disk substrate on which a thin (<100 micron) film of mercury is electrodeposited. Two types of MFE substrates are commonly used, both with inherent problems. The first type of substrate consists of inert materials, such as glassy carbon, graphite or carbide, upon all of which a "mercury droplet film" forms. Even though these types of electrodes have been successfully used for many years in quantitative work, their characteristics are far from ideal. The second type of substrate consists of metals, such as platinum, gold or silver, all of which have a tendency to dissolve into the mercury and to form intermetallic compounds with the metals being analyzed or to eventually convert the film into an amalgam-film, severely limiting the utility of such electrodes.

Although similar to the other noble metals, iridium is substantially harder, more inert, and more expensive. Because of these properties, iridium has generally been overlooked as an electrode substrate. About seven years ago, Kounaves et al. (J. Electrochem. Soc., Vol. 133, pp. 2495-2498 (1986); and J. Electroanal. Chem., Vol. 216, pp. 53-69 (1987)) showed that iridium possesses two properties which make it ideal as a mercury electrode substrate: (1) its solubility in mercury is below $10^{-6}$ percent by weight; and (2) mercury can be electroplated onto an iridium disk to give a uniform film or hemispherical coverage.

Ultramicroelectrodes are electrodes which have a dimension of less than 20 microns in size. They have been shown to possess several unique characteristics in terms of mass transport rates, capacitive charging RC, and reduction in IR drop. They have rapidly become invaluable in a wide range of applications. As with larger electrodes, the most common materials used in their preparation have been platinum, gold or carbon fiber. Platinum ultramicroelectrodes have been fabricated down to diameters as small as 0.003 micron and in various geometries, such as disk, cylindrical and conical. Typical carbon fiber electrodes have diameters in the range of 5-20 microns and are similarly used either as fibers of 1-5 mm length or as disks.

Attempts at fabricating mercury ultramicroelectrodes both on solid substrates and in bulk form have been made by several groups; however, many of the same problems that have plagued the larger electrodes have also limited the utility of the ultramicroelectrodes. The development of iridium-based mercury ultramicroelectrodes was hampered by the lack of commercial available iridium wire of sufficiently small diameter (caused by difficulties in drawing iridium to <127 microns) and the ineffectiveness of the typical etching solutions normally used for platinum or gold.

In J. Electroanal. Chem, Vol. 301, pp. 77-85 (1991), which is incorporated herein by reference, Kounaves et al. describe how they overcame the etching problems with iridium and were successful in developing iridium based mercury ultramicroelectrodes with diameters of 1 to 10 microns. They demonstrated that a stable mercury hemisphere could be formed on the iridium surface and that, by using ASV, the detection of $Cd^{+2}$ at $10^{-8}M$ with an analysis time of less than 1 second was feasible.

One disadvantage associated with single ultramicroelectrodes is that they produce currents in the picoamp or nanoamp range and thus usually require specialized instrumentation for reliable measurements. To overcome this limitation, many types of electrode assemblies comprising multielement ultramicroelectrode array configurations have been developed.

Some of the earliest "electroanayltically based" fabrication and experimental work using the disk microelectrode array concept was reported by Gueshi et al., J. Electroanal. Chem., Vol. 89, pp. 247-260 (1978). To confirm their theory for chronopotentiometry and chronoamperometry at partially covered electrodes (i.e., in effect, an array of microelectrodes), they used a gold electrode covered with a photoresist layer. A photolithographic process and mask for the array pattern was used to give a hexagonal array of exposed "gold microelectrodes" on the electrodes surface. Aoki et al., J. Electroanal. Chem., Vol. 125, pp. 315-320 (1981), used a similar technique to produce, on a large glassy carbon substrate, arrays of 157, 114, 51, and 25 circular microelectrodes with radii of 20, 40, 100 and 200 microns, respectively. Caudill et al., Anal. Chem. Vol. 544, pp. 2532-2535 (1982), constructed an electrode array using 5 rows of 20 carbon fibers sandwiched between glass slides, resulting in 10 micron diameter disks. The electrode was used as a channel-type amperometric flow cell detector. Sleszynski et al., Anal. Chem., Vol. 56, pp. 130-135 (1984), used epoxy filled reticulated vitreous carbon (RVC) to construct a two dimensional random order microelectrode array that yielded nearly steady-state currents. Hepel et al., J. Electrochem. Soc. Vol. 133, pp. 752-757 (1986), made Cr and Au microelectrode arrays with over 1 million active electrodes on a 1 $cm^2$ area, each of 0.75 micron diameter, using electron beam lithography and polymethylmethacrylate resist. Finally, several groups have used porous materials such as polycarbonate membrane or aluminum oxide films to fabricate either recessed random "microhole" arrays, or, in one case, to electrodeposit platinum into the pores resulting in random ordered 0.1 micron disk microelectrodes.

Band arrays, which are also referred to as line or linear microelectrode arrays, have one of their dimensions in the micro-sized domain, while the other dimension may be several orders of magnitude larger. They have usually been fabricated either by sandwiching a thin metal layer between glass layers and then polishing one end or by photolithography.

Band microelectrodes made of metals such as Pt, Au, or Cr are, of course, not amenable for use as substrates for mercury film formation, since coverage of such a long line would require amalgamation, which is undesirable. Mercury deposition on non-metal band microelectrodes would result in a long column of easily detachable small mercury drops, again totally undesirable.

There are several key points in regards to microelectrode arrays reported in the literature. First, a large number of the "microelectrode arrays" are actually linear "arrays" of interdigitated line/band microelectrodes. Second, one of the greatest drawbacks with all of these microelectrode arrays is that their microelectrode surfaces cannot effectively be renewed chemically or by polishing.

In Proceedings of the 12th International Conference of the Association for the Advancement of Rehabilitation Technology, New Orleans, La., pp. 292-293 (June 1989) and Technology Development for a Chronic Neural Interface, Ph.D. Dissertation, Stanford University, Technical Report No. E073-1 (August 1990), which are incorporated herein by reference, Kovacs et al. disclose an implantable electrode assembly which includes an array of iridium ultramicroelectrodes useful as a direct interface between the human nervous system and external prosthetic devices. The iridium ultramicroelectrode array is formed on a suitable substrate by a photolithographic technique with a specialized lift-off patterning process.

None of the above-described ultramicroelectrode arrays involve mercury plated films/spheres and/or have been used for metal ion determination.

SUMMARY OF THE INVENTION

It is an object of the present invention to provide a new and novel electrode assembly.

It is another object of the present invention to provide an electrode assembly as described above which may be used to quantify the levels of various metals in an aqueous solution.

Therefore, an electrode assembly constructed in accordance with the teachings of the present invention and in accordance with the objects broadly set forth above is provided herein, the electrode assembly comprising an array of ultramicroelectrodes arranged on a suitable substrate, each of the ultramicroelectrodes comprising a layer of iridium and a layer of mercury, the mercury layer being deposited on the iridium layer.

In a preferred embodiment, the substrate comprises a wafer of doped silicon on which a dielectric layer of silicon dioxide has been grown. A plurality of bond pads and corresponding interconnect traces are formed on the dielectric layer of silicon dioxide using microphotolithography. A corresponding plurality of iridium deposits are then patterned on the interconnect traces at predetermined locations using microphotolithography. A low-temperature plasma deposition technique is next used to apply a passivation layer to the finished metallization to electrically insulate it from external solutions. Plasma etching into the passivation layer is then used to expose selected portions of the iridium deposits and bond pads. Wires may be bonded to the exposed portions of the bond pads to permit external electrical connections to the assembly. Just before use, mercury is electroplated onto the exposed portions of the iridium deposits to form iridium based mercury ultramicroelectrodes.

The above-described electrode assembly may be used in conjunction with a reference electrode and a potentiostat to perform various electrochemical techniques, such as linear or square wave voltammetry, so as to provide qualitative or quantitative measurements of metals in aqueous solution.

One advantage to the above-described electrode assembly, as compared to single ultramicroelectrodes, is that it multiplies a current signal many times over, thereby permitting the use of less sophisticated commercially available instrumentation than would otherwise be possible. Another advantage to the above-described electrode assembly is that it achieves a substantial improvement over existing devices with respect to signal-to-noise ratio. Still another advantage to the above-described electrode assembly is that it is stable and rugged enough to withstand the procedures necessary for in-situ trace metal determination, such as in the remote sensing of groundwater contaminates.

The present invention is directed to a method of making an electrode assembly comprising the steps of a) providing a substrate having a non-conductive top surface; b) depositing iridium onto the non-conductive top surface of the substrate; and c) depositing a quantity of mercury onto at least a portion of the iridium deposit.

The present invention is also directed to a field deployable sensor which includes the above-described electrode assembly.

Additional objects, features and advantages of the present invention will be set forth in part in the description which follows, and in part will be obvious from the description or may be learned by practice of the invention. The objects, features and advantages of the invention may be realized and attained by means of the instrumentalities and combinations particularly pointed out in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings wherein like reference numerals represent like parts.

DETAILED DESCRIPTION OF PREFERRED EMBODIMENTS

Figure 1:
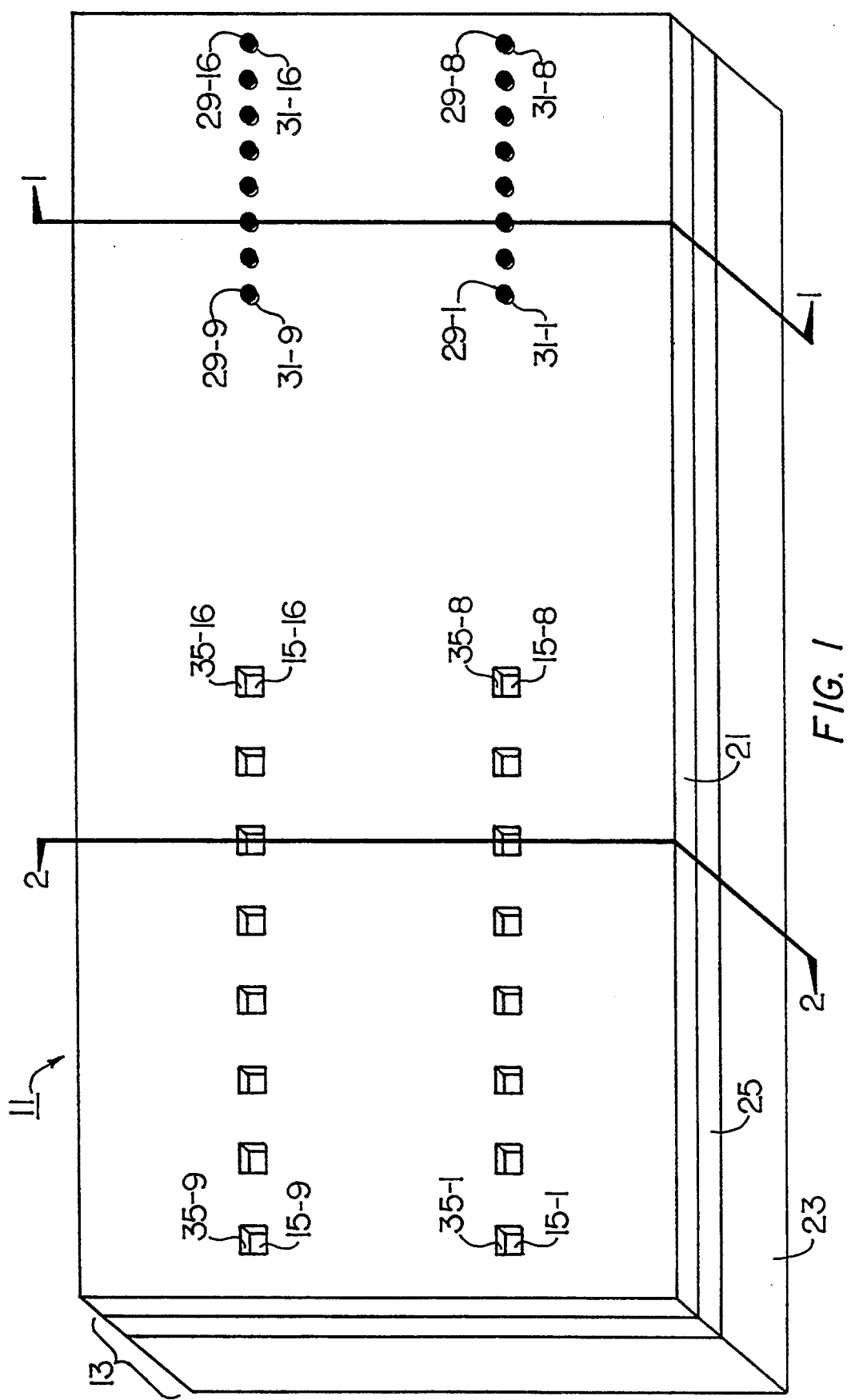
FIG. 1 is a top perspective view of one embodiment of an electrode assembly adapted for use in quantifying the levels of various metals in an aqueous solution, the electrode assembly being constructed according to the teachings of the present invention.
Figure 2:
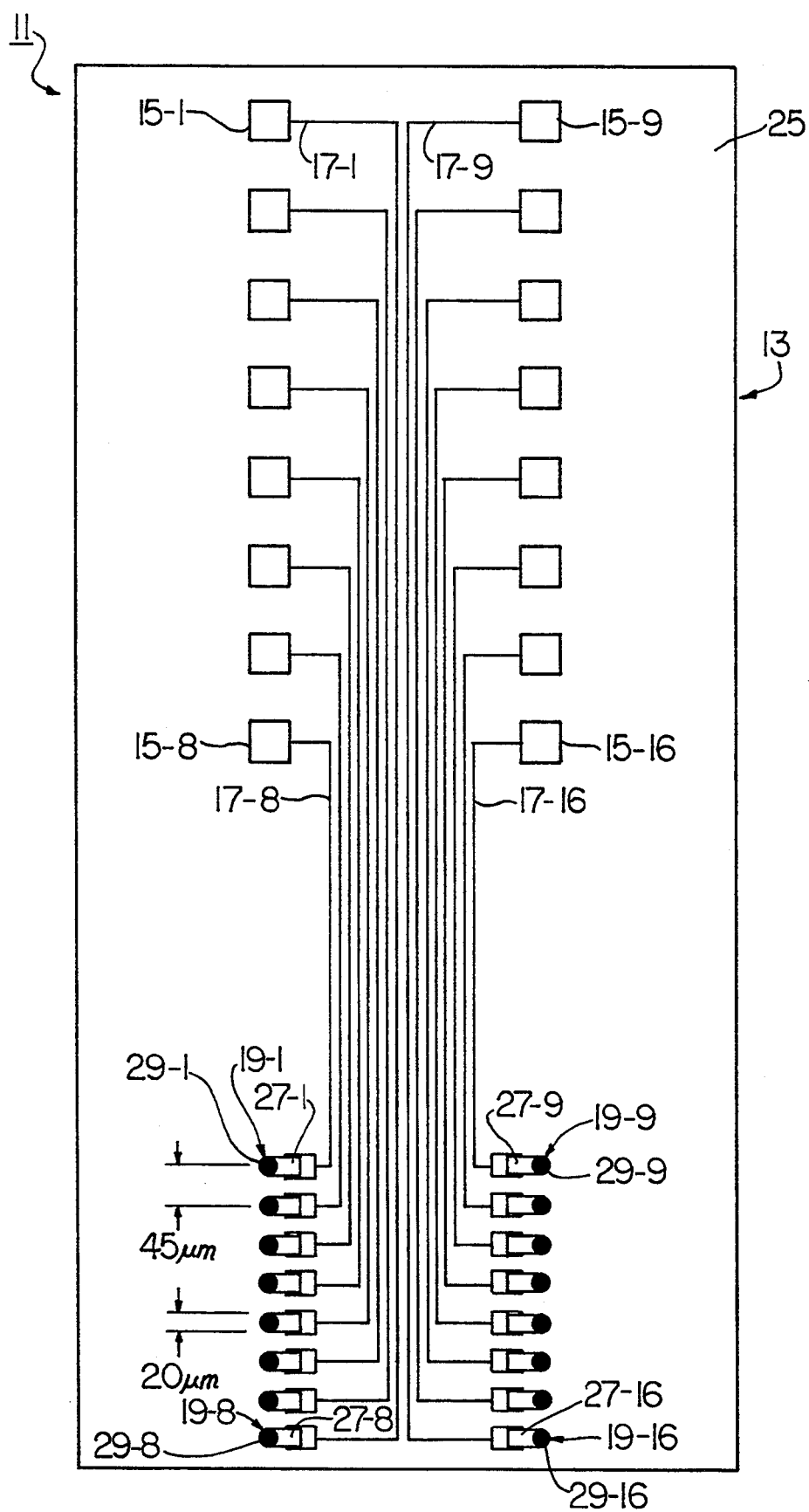
FIG. 2 is a schematic top view of the electrode assembly shown in FIG. 1 with the passivation layer not being shown to reveal the components covered thereby.
Figure 3:
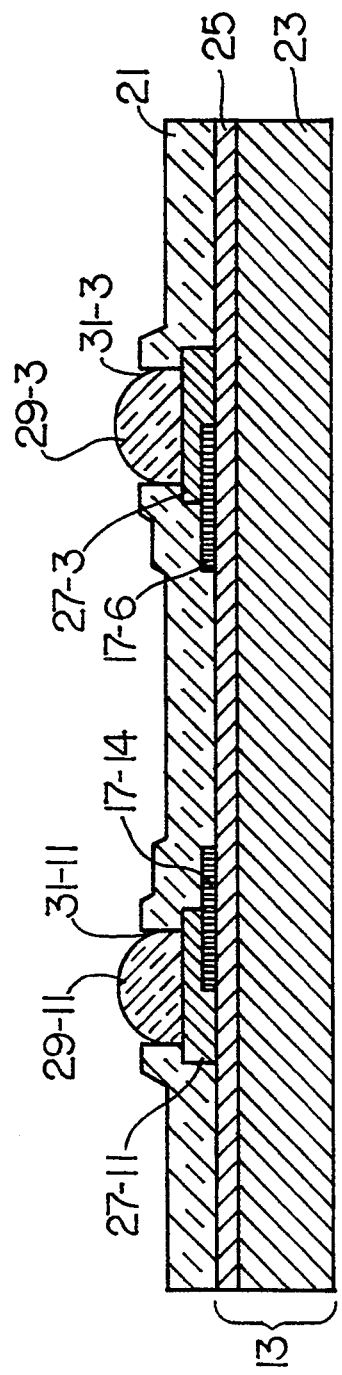
FIG. 3 is a section view of the electrode assembly shown in FIG. 1 taken along line 1—1.
Figure 4:
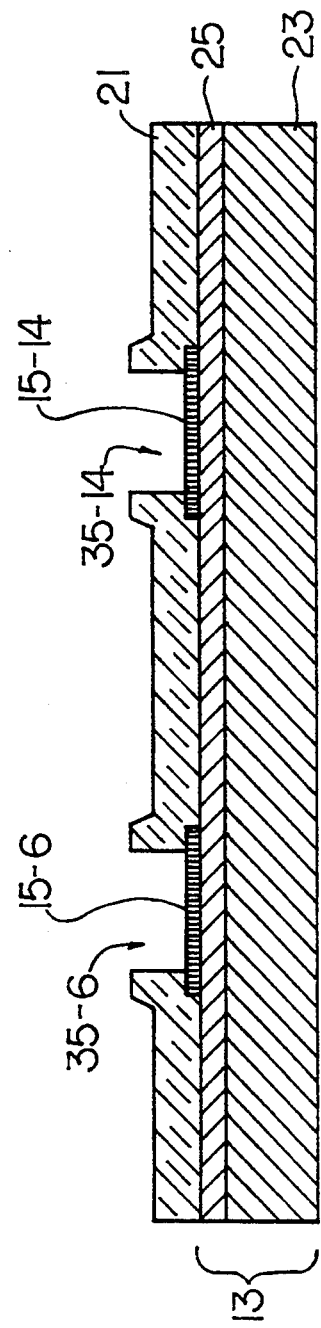
FIG. 4 is a section view of the electrode assembly shown in FIG. 1 taken along line 2—2.

Referring now to FIGS. 1 through 4, there are shown various views of one embodiment of an electrode assembly adapted for use in quantifying the levels of various metals in an aqueous solution, the electrode assembly being constructed according to the teachings of the present invention and represented generally by reference numeral 11.

Assembly 11 includes a substrate 13, a plurality of bond pads 15-1 through 15-16, a plurality of interconnects 17-1 through 17-16, a plurality of iridium-based mercury ultramicroelectrodes 19-1 through 19-16, and a passivation layer 21.

Substrate 13 includes a lower layer 23 of conductive material and an upper layer 25 of insulative material. Preferably, layer 23 comprises a chip or wafer of doped silicon, and layer 25 comprises a layer of silicon dioxide or another insulator, such as silicon nitride, which has been grown or deposited on the doped silicon (to a thickness of approximately 0.5–1.0 microns). Instead of using a lower layer of conductive material and an upper layer of insulative material, a single layer of non-conductive material, such as sapphire or glass, also may be used as the substrate; however, the former arrangement is preferred because doped silicon can additionally accommodate active microelectronic circuits, e.g., signal processing electronics, on-chip potentiostats, signal sources, amplifiers, current-to-voltage converters, and the like. In this way, voltammetric measurements can be performed on-chip.

Bond pads 15-1 through 15-16, which are preferably made of gold, and interconnects 17-1 through 17-16, which are also preferably made of gold, are preferably deposited on upper layer 25 of substrate 13 according to the following microphotolithographic process: First, the sample is coated with hexamethyl disilazane (spun dry), followed by 1 micron of Shipley 1370-27 photoresist (Shipley Company, Inc., Newton, Mass.) spun on at 3500 rpm. The sample is permitted to air dry for 20 minutes, is oven baked for 5 minutes at 90 degrees Celsius, and is then permitted to cool for 5 minutes.

The sample is then soaked in chlorobenzene for 13 minutes, blown dry with nitrogen, and oven baked for 20 minutes at 90 degrees Celsius.

The photoresist is then exposed with an appropriate metallization pattern mask (dark field). Current exposure times are 20–30 seconds on the Kasper 2001 contact aligner (U.V. dose 45–55 mJ/cm$^2$).

The photoresist is then immersion developed in AZ-351 concentrate which has been diluted to 1 part in 5 with deionized water for 90–120 seconds and then rinsed in deionized water for 5 minutes. The resulting photoresist lip is then optically inspected (it should be approximately 1 micron wide). The sample is then oxygen de-scummed in the Drytek DRIE-100 for 3 minutes at a pressure of 150 mTorr, with a gas flow of 100 sccm O$_2$, using 300 W forward RF power.

300 Å of titanium and then 5000 Å of gold at 5–10 Å/second are vacuum deposited onto the sample from an electron-gun source oriented perpendicularly relative to the sample. The titanium (not shown) serves as an adhesion layer for bonding the gold bond pads 15 and interconnects 17 onto upper layer 25 of substrate 13.

The sample is then soaked in acetone for 5 minutes. Excess material is removed with acetone using a pressure sprayer, followed by an ultrasonic clean in acetone for 2–3 minutes. The residual acetone is rinsed off with isopropyl alcohol and the sample is blown dry with nitrogen. The metallization is then inspected, with the edges of the metal lines being checked for "spikes" and the traces being checked for breaks or short-circuits.

Bond pads 15-1 through 15-16 are preferably 500 microns $\times$ 500 microns in size and are separated from one another by 500 microns to permit manual attachment of wires thereto using conductive epoxies. Alternatively, because they are made of gold, conventional ultrasonic wire bonding may be used.

Ultramicroelectrodes 19-1 through 19-16, each of which is formed from a combination of iridium and mercury, are prepared in the following manner:

First, iridium deposits 27-1 through 27-16 are formed on the free ends of interconnects 17-1 through 17-16, respectively, using the microphotolithographic process described above. In the present embodiment, each iridium deposit 27 has a thickness of approximately 3500 Å (which is deposited at a rate of 1–3 Å/second) and is adhered with 150 Å of titanium.

Next, passivation layer 21 is applied to the top surface of the sample as follows: First, the sample is oxygen-plasma cleaned (to remove organic residues) in the Drytek DRIE-100 for 5 minutes at a pressure of 100 mTorr, using a gas flow of 100 sccm of O$_2$, and 500 W of RF power. Next, 1 micron of silicon nitride is plasma deposited in a PWS reactor (Pacific Western Systems, Inc., Mountain View, Calif.) for 45 minutes at 345 degrees Celsius, at a pressure of 2.0 Torr, using gas flows of 265 sccm of SiH$_4$ (26.0% on mass-flow controller) and 1500 sccm NH$_3$ (18.8% on the mass-flow controller) with 30 W of RF power at 100 KHz. An ellipsometer is then used to verify that the film thickness is 1.0$\pm$0.1 micron and that it has a refractive index of 2.05$\pm$0.05.

Openings 31-1 through 31-16 are then plasma etched into passivation layer 21 to expose portions of iridium deposits 27-1 through 27-16, respectively, so as to permit the electroplating of mercury thereonto. In the present embodiment, openings 31 are circular in cross-section and have a diameter of approximately 20 microns. Plasma etching may be performed according to the following process: First, the sample is coated with HMDS (spun dry), followed by 0.75 micron Hoechst AZ-1811 photoresist (spun on at 4000 RPM), and is then oven baked for 30 minutes at 90 degrees Celsius.

The sample is then aligned and exposed using a passivation opening mask (dark field) for 30 seconds on a Kasper 2001 contact aligner (U.V. dose=55 mJ/cm$^2$).

The photoresist is then immersion developed in MIF-319 developer for 30 seconds, rinsed in deionized water for 5 minutes, blown dry with nitrogen and inspected optically.

The sample is then oven baked for 30 minutes at 110 degrees Celsius (to improve adhesion of photoresist to the nitride and to reduce undercutting during plasma etching of the nitride).

The passivation layer is then plasma etched in a Drytek DRIE-100 for 20 minutes at a pressure of 150 mTorr, using gas flows of 50 sccm of $C_2ClF_5$ and 50 sccm of $SF_6$, at 300 W of RF power. The openings are then inspected optically.

The photoresist is then plasma stripped with $O_2$ in a Matrix plasma etcher (Matrix Integrated Systems, Richmond, Calif.) for 90 seconds and spun dry to remove soluble inorganic residues.

Figure 5B:
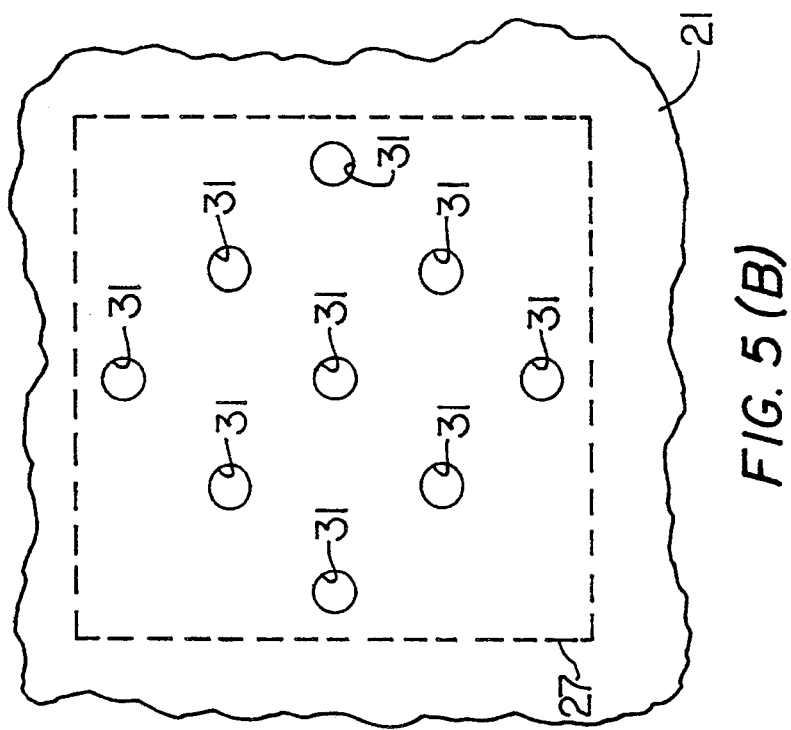
FIGS. 5(a) and 5(b) are schematic fragmentary top views illustrating either a single opening or a plurality of openings etched into the passivation layer covering an iridium deposit in the preparation of either a single iridium based mercury ultramicroelectrode or a plurality of iridium based mercury ultramicroelectrodes, respectively.
Figure 5A:
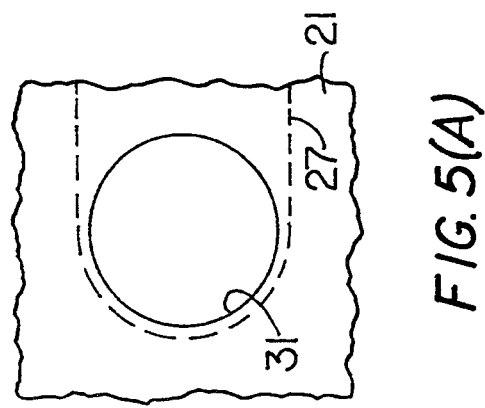

As can be seen in FIG. 5(a), each opening 31 is preferably dimensioned relative to its underlying iridium deposit 27 so that a rim of passivation layer 21 covering the iridium deposit 27 is left around the opening 31 to decrease the likelihood of delamination of the metal or leakage of ions under the passivation layer (and into the dielectric layer, which may be a material in which some ions can readily diffuse, such as silicon dioxide).

It should be understood that, whereas in the present embodiment only one opening is etched into the passivation layer covering an iridium deposit for use in making a single ultramicroelectrode, one could plasma etch an array of openings into the passivation layer covering an iridium deposit for use in making an array of ultramicroelectrodes (see, for example, FIG. 5(b)).

Plasma etching as described above can also be used to create openings 35-1 through 35-16 in the passivation layer 21 covering bond pads 15-1 through 15-16 so as to permit wires to be bonded to thereto for connection to external electronics. (Preferably, only a portion of each bond pad 15 is exposed by plasma etching and a passivation rim is left around the exposed portion.)

Just before assembly 11 is intended for use, the above described device is mounted on an appropriate printed circuit board or similar holder and ultramicroelectrodes 19-1 through 19-16 are completed by electroplating mercury deposits 29-1 through 29-16 onto the exposed disk-shaped portions of iridium deposits 27-1 through 27-16, respectively. The geometry of the deposited mercury can be controlled from a thin film to almost a sphere depending on the deposition parameters. Because of its ruggedness and stability, a hemispherical geometry is preferred. To deposit a hemisphere of mercury onto an exposed iridium disk having a radius of approximately 10 microns, the ultramicroelectrode array portion of the above-assembled device is immersed in a solution containing 0.1 mol/L of $HClO_4$ and $8 \times 10^{-3}$ mol/L of $Hg(NO_3)_2$, and a coulometric deposition at $-200$ mV vs. a sodium saturated calomel electrode (SSCE) is used to apply a charge of 95 microcoulombs (15 minutes). For optimum performance, the mercury deposits should be newly replating every day even though, when stored in deionized water with 0.1 mol/L $KNO_3$ and application of a slight negative potential of about $-50$ mV, it can be maintained for more than a week. After deposition with mercury, the assembly is removed from the deposition solution, rinsed carefully with deionized water, and transferred to a sample cell.

It is to be understood that the number, size and arrangement of ultramicroelectrodes 19-1 through 19-16 as shown in the drawings and as described herein are merely exemplary. It is also to be understood that the method of manufacturing assembly 11 as set forth above is also merely exemplary.

Assembly 11 may be used in the conventional manner to perform square wave anodic stripping voltammetry or other electrochemical techniques. Advantageously, because of the unique characteristics of high mass transport and the steady-state diffusional flux associated with assembly 11, the sample solutions being tested do not require stirring during the preconcentration step, and no equilibration period is needed before initiating the anodic scan.

EXAMPLE

Figure 6:
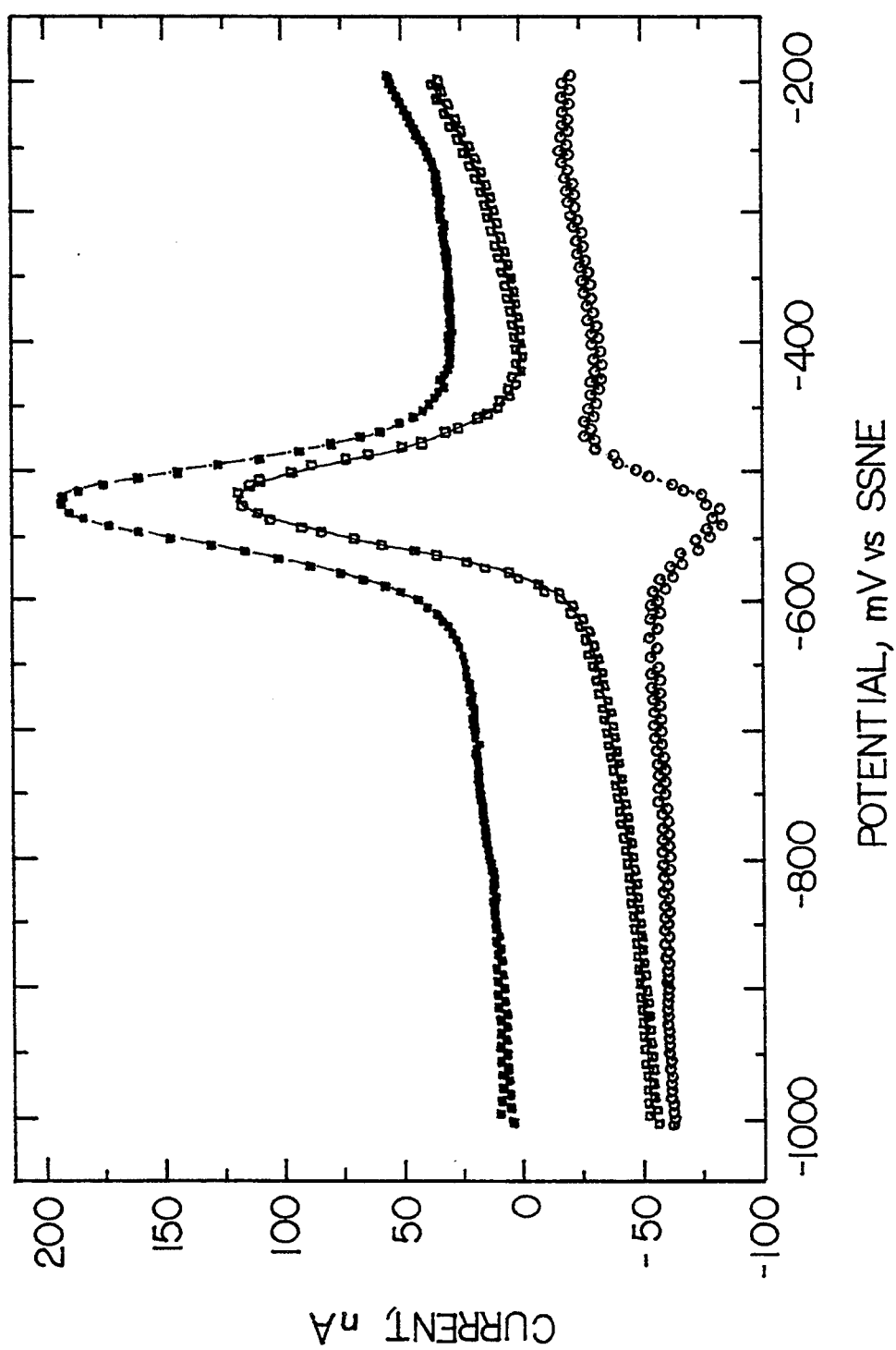
FIG. 6 is a graphic representation of the square wave anodic stripping voltammetry measurements performed using the electrode assembly shown in FIG. 1.

Square wave anodic stripping voltammetry (SWASV) was performed on a sample solution containing $1 \times 10^{-6}$ mol/L of $Pb(NO_3)_2$ in 0.1 mol/L of acetate buffer solution using assembly 11, a custom-made, solid-state Nafion-coated Ag/AgCl reference electrode (SSNE) containing no internal liquid electrolyte or flow junctions, and an EG&G PAR Model 273 potentiostat/galvanostat (EG&G PAR, Princeton, N.J.) interfaced to an IBM PS/2-30286 with custom control software. The preconcentration was carried out with a SW amplitude of 25 mV, a SW step height of 5 mV and a SW frequency of 240 Hz. FIG. 6 shows the forward (-□-), reverse (-O-), and net (- -) SWASV response obtained for the above system.

Figure 7:
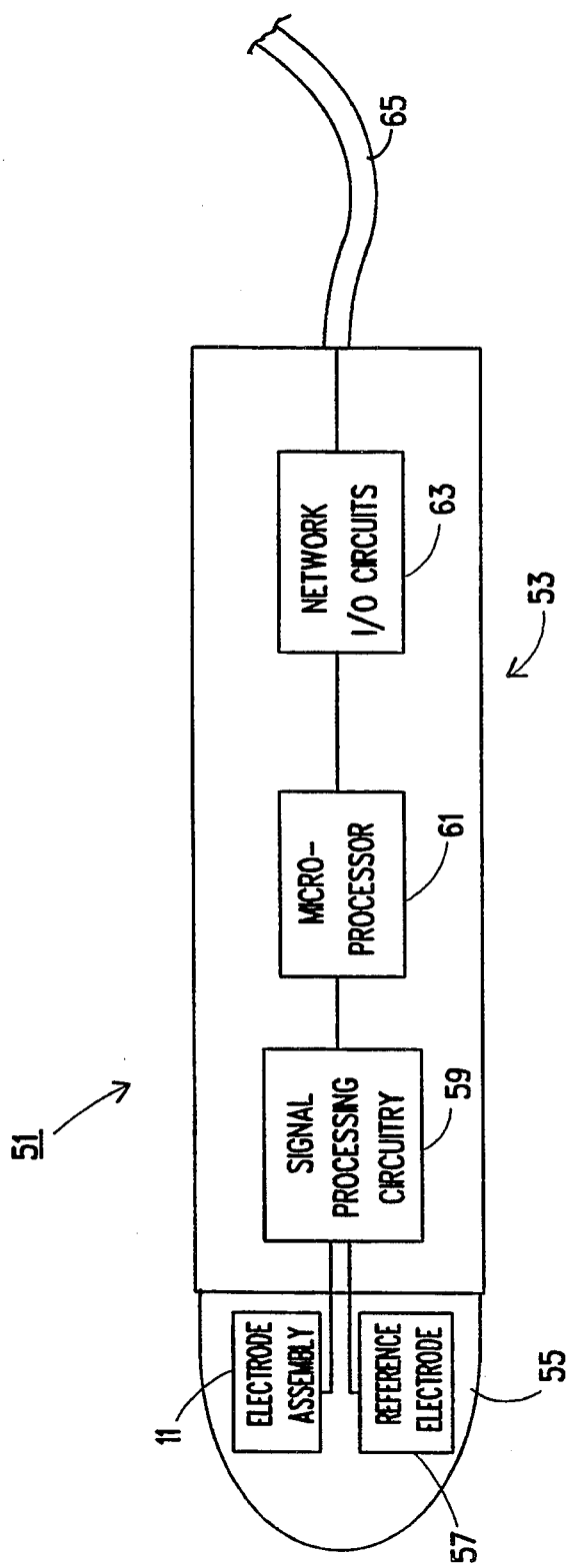
FIG. 7 is a block diagram of one embodiment of a field deployable sensor constructed according to the teachings of the present invention.

Referring now to FIG. 7, there is shown a block diagram of a field deployable sensor constructed according to the teachings of the present invention, the sensor being represented generally by reference numeral 51.

Sensor 51 includes a cigar-shaped casing 53, casing 53 including a removably mounted tip 55. Tip 55 is porous to water to permit sampling thereof in the manner to be described below.

Sensor 51 also includes an electrode assembly 11 and a reference electrode 57. Assembly 11 and reference electrode 57 are disposed within tip 55 so that water passing through tip 55 may be sampled thereby.

Sensor 51 additionally includes signal processing circuitry 59 (including a potentiostat, various filters and the like), a microprocessor 61, and network interconnect circuitry 63.

Sensor 51 further includes a cable 65 for electrically connecting the electronics of sensor 51 to a computer or the like at a remote location. Cable 65 also may be used to lower casing 53 into a borehole and may be provided with convenient depth markings to permit depth measurement.

As can readily be appreciated, a network of sensors 51 lowered into different boreholes could be used to measure or to track underground flows of hazardous materials.

As can also be readily appreciated, sensor 51 could be provided with two or more electrode assemblies 11 that could be individually used in those instances in which a "fresh" electrode is required. Simple circuitry could be used to choose which electrode assembly 11 would be used at a given time. Alternatively, sensor 51 could be made to be multi-functional by providing a variety of different types of electrodes (or detectors) within casing 53. For example, in addition to including assembly 11, sensor 51 could also be provided with a thermometer and/or a radiation detector.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. An electrode assembly for use in quantifying the levels of various metals in an aqueous solution, said electrode assembly comprising:
   a) a substrate; and
   b) an array of ultramicroelectrodes arranged on said substrate, each of said ultramicroelectrodes comprising a layer of iridium and a layer of mercury, said mercury layer being disposed on said iridium layer.

2. The electrode assembly as claimed in claim 1 wherein said substrate has a non-conductive top surface and wherein said ultramicroelectrodes are arranged on said non-conductive top surface.

3. The electrode assembly as claimed in claim 2 wherein said substrate is a quantity of doped or undoped silicon upon which a layer of silicon dioxide or silicon nitride has been grown or deposited.

4. The electrode assembly as claimed in claim 1 further comprising means for interconnecting said ultramicroelectrodes to external electronics.

5. The electrode assembly as claimed in claim 4 wherein said interconnecting means comprises a plurality of interconnect traces and bond pads arranged on said substrate.

6. The electrode assembly as claimed in claim 5 wherein said interconnect traces and bond pads are made of gold.

7. The electrode assembly as claimed in claim 1 wherein said mercury layer is hemispherical or any other shape.

8. The electrode assembly as claimed in claim 1 wherein said iridium layer of two or more of said array of ultramicroelectrodes is formed from a single iridium deposit.

9. The electrode assembly as claimed in claim 1 wherein all of said ultramicroelectrodes are identical to one another.

10. The electrode assembly as claimed in claim 9 wherein two or more of said ultramicroelectrodes are electrically interconnected.

11. The electrode assembly as claimed in claim 10 wherein said ultramicroelectrodes have non-overlapping diffusion fields.

12. The electrode assembly as claimed in claim 9 wherein said ultramicroelectrodes have non-overlapping diffusion fields.

13. A method of making an electrode assembly comprising the steps of:
   a) providing a substrate, said substrate having a non-conductive top surface;
   b) depositing iridium onto said non-conductive top surface of said substrate; and
   c) depositing a quantity of mercury onto at least a portion of said iridium deposit.

14. The method as claimed in claim 13 wherein said mercury depositing step comprises electroplating said quantity of mercury onto said portion of said iridium deposit.

15. A method of making an electrode assembly comprising the steps of:
   a) providing a substrate, said substrate having a non-conductive top surface;
   b) forming an array of iridium ultramicroelectrodes on said non-conductive top surface of said substrate; and
   c) depositing a quantity of mercury on said iridium ultramicroelectrodes.

16. The method as claimed in claim 15 further comprising, prior to said iridium ultramicroelectrodes forming step, the step of forming an array of bond pads and interconnect traces on said non-conductive top surface of said substrate, wherein said iridium ultramicroelectrodes are formed at predefined locations on said interconnect traces.

17. An electrode assembly manufactured by the method of claim 15.

18. The method as claimed in claim 15 wherein said bond pads and said interconnect traces are made of gold.

19. The method as claimed in claim 15 wherein said bond pads, said interconnect traces and said iridium ultramicroelectrodes are deposited by microphotolithography.

20. An electrode assembly manufactured by the method of claim 19.

21. The method as claimed in claim 15 further comprising, prior to said mercury depositing step, the steps of depositing a passivation layer over the finished metallization and then exposing at least a portion of each of said iridium ultramicroelectrodes and said bond pads, wherein said deposited mercury is deposited over said exposed portions of said iridium ultramicroelectrodes.

22. An electrode assembly manufactured by the method of claim 21.

23. A portable sensor adapted to detect the levels of metals in an aqueous solution, said portable sensor comprising:
   a) an elongated housing having a porous tip for permitting the passage therethrough of the aqueous solution being tested;
   b) an electrode assembly appropriately disposed within said elongated housing to sample the aqueous solution, said electrode assembly comprising
      i) a substrate; and
      ii) an array of ultramicroelectrodes arranged on said substrate, each of said ultramicroelectrodes comprising a layer of iridium and a layer of mercury, said mercury layer being disposed on said iridium layer;
   c) a reference electrode appropriately disposed within said elongated housing to sample the aqueous solution; and
   d) electronics disposed within said elongated housing for performing simple or pulsed voltammetric techniques such as anodic stripping voltammetry.

24. The field deployable sensor as claimed in claim 23 further comprising a cable connected to said electronics for transmitting the results of said electrochemical measurements to a nearby or remote location.

* * * * *